(12) United States Patent
Autebert et al.

(10) Patent No.: US 10,549,276 B2
(45) Date of Patent: Feb. 4, 2020

(54) MICROFLUIDIC PROBE HEAD FOR PROVIDING A SEQUENCE OF SEPARATE LIQUID VOLUMES SEPARATED BY SPACERS

(71) Applicant: International Business Machines Corporation, Armonk, NY (US)

(72) Inventors: Julien Autebert, Kilchberg (CH); Emmanuel Delamarche, Thalwil (CH); Govind Kaigala, Rueschlikon (CH); Aditya Kashyap, Zürich (CH); Xander Frank Van Kooten, Adliswil (CH)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/519,049

(22) Filed: Jul. 23, 2019

(65) Prior Publication Data
US 2019/0344268 A1 Nov. 14, 2019

Related U.S. Application Data

(63) Continuation of application No. 15/041,088, filed on Feb. 11, 2016, now Pat. No. 10,391,488.

(30) Foreign Application Priority Data

Feb. 13, 2015 (EP) .................................... 15155056

(51) Int. Cl.
*G01N 35/08* (2006.01)
*G01N 1/28* (2006.01)
(Continued)

(52) U.S. Cl.
CPC ....... *B01L 3/502715* (2013.01); *B01L 3/0262* (2013.01); *B01L 3/0293* (2013.01);
(Continued)

(58) Field of Classification Search
CPC ....... B01L 3/502715; B01L 2200/0673; B01L 2200/0621; G01N 2035/1034; G01N 1/28; G01N 35/10
See application file for complete search history.

(56) References Cited

U.S. PATENT DOCUMENTS

| | | | |
|---|---|---|---|
| 8,062,903 B2 | 11/2011 | Chiu | |
| 10,391,488 B2 * | 8/2019 | Autebert | ................ G01N 35/08 |

(Continued)

FOREIGN PATENT DOCUMENTS

| | | |
|---|---|---|
| CN | 103140283 A | 6/2013 |
| GB | 2474228 A | 4/2011 |

(Continued)

OTHER PUBLICATIONS

First Office Action, dated Jan. 3, 2019 for CN Application CN201680010008.3, 8 pages.
(Continued)

*Primary Examiner* — Lyle Alexander
*Assistant Examiner* — Bryan Kilpatrick
(74) *Attorney, Agent, or Firm* — Michael A. Petrocelli

(57) ABSTRACT

A microfluidic probe head for providing a sequence of separate liquid volumes separated by spacers, the separate liquid volumes including a respective target substance associated with a respective target area, the microfluidic probe head including an inlet and an outlet; a first fluid channel fluidly connected to the inlet, the first fluid channel configured for delivering an injection liquid from the inlet to a respective target area; a second fluid channel fluidly connected to the outlet, the second fluid channel configured for delivering liquid volumes from the respective target area to the outlet; and a spacer insertion unit fluidly connected to the second fluid channel, the spacer insertion unit configured for inserting spacers into the second fluid channel between the
(Continued)

liquid volumes to provide the sequence of separate liquid volumes separated by spacers.

15 Claims, 4 Drawing Sheets

(51) Int. Cl.
    | | |
    |---|---|
    | *G01N 35/10* | (2006.01) |
    | *G01N 1/02* | (2006.01) |
    | *B01L 3/00* | (2006.01) |
    | *B01L 3/02* | (2006.01) |

(52) U.S. Cl.
    CPC .......... *B01L 3/502784* (2013.01); *G01N 1/28* (2013.01); *G01N 35/08* (2013.01); *B01L 2200/0621* (2013.01); *B01L 2200/0636* (2013.01); *B01L 2200/0673* (2013.01); *B01L 2300/089* (2013.01); *B01L 2300/0861* (2013.01); *B01L 2400/0478* (2013.01); *B01L 2400/0484* (2013.01); *B01L 2400/0487* (2013.01); *B01L 2400/086* (2013.01); *G01N 35/10* (2013.01); *G01N 2001/028* (2013.01)

(56) References Cited

U.S. PATENT DOCUMENTS

| | | |
|---|---|---|
| 2007/0039866 A1 | 2/2007 | Schroeder |
| 2009/0217742 A1 | 9/2009 | Chiu |
| 2010/0252118 A1 | 10/2010 | Fraden |
| 2013/0281316 A1 | 10/2013 | Ismagilov |
| 2013/0333761 A1 | 12/2013 | Delamarche |
| 2016/0236194 A1 | 8/2016 | Autebert |

FOREIGN PATENT DOCUMENTS

| | | |
|---|---|---|
| WO | 2006014460 A1 | 2/2006 |
| WO | 2012056369 A1 | 5/2012 |

OTHER PUBLICATIONS

International Search Report and Written Opinion, International Application No. PCT/EP2016/052996, International Filing Date Feb. 12, 2016, 10 pages.

List of IBM Patents or Patent Applications Treated as Related. 2 pages.

* cited by examiner

MICROFLUIDIC PROBE HEAD FOR PROVIDING A SEQUENCE OF SEPARATE LIQUID VOLUMES SEPARATED BY SPACERS

BACKGROUND

The invention relates to a microfluidic probe head, a microfluidic probe including the microfluidic probe head, and a method for providing a sequence of separate liquid volumes separated by spacers.

Microfluidics deals with the behavior, precise control and manipulation of small volumes of fluids that are typically constrained to micrometer-length scale channels and to volumes typically in the sub-milliliter range. Here, fluids refer to liquids and either term can be used interchangeably in the rest of the document. In particular, typical volumes of fluids in microfluidics range from $10^{-15}$ L to $10^{-5}$ L and are transported via microchannels with a typical diameter of $10^{-7}$ m to $10^{-4}$ m.

At the microscale, the behavior of the fluids can differ from that at a larger, i.e. macroscopic, scale. In particular, surface tension, viscous energy dissipation and fluidic resistance are dominant characteristics of the flow. For example, the Reynolds number, which compares an effect of momentum of a fluid to the effect of viscosity, can decrease to such an extent that the flow behavior of the fluid becomes laminar rather than turbulent.

Fluids do not necessarily mix in the traditional, chaotic sense at the microscale due to the absence of turbulence in low-Reynolds number flows. Interfacial transport of molecules or small particles between adjacent fluids often takes place through diffusion. As a consequence, certain chemical and physical properties of fluids such as concentration, pH, temperature and shear force are deterministic. This provides more uniform chemical reaction conditions and higher grade products in single and multi-step reactions.

A microfluidic probe is a device, in particular a microfabricated scanning device, for depositing, retrieving, transporting, delivering, and/or removing liquids, in particular liquids containing chemical and/or biochemical substances. For example, the microfluidic probe can be used on the fields of diagnostic medicine, pathology, pharmacology and various branches of analytical chemistry. A microfluidic probe can for instance be used for performing molecular biology procedures for enzymatic analysis, deoxyribonucleic acid (DNA) analysis and proteomics.

Retrieving substances from surfaces is important for numerous applications in diagnostics, pharmaceutical and life science research. When substances need to be recovered from different areas, this likely leads to a diffusion of analytes away from their initial recovery volume in the next recovered volume from another area, which potentially causes cross-contaminations between sequentially recovered segments of liquid.

SUMMARY

According to a first aspect, the invention can be embodied as a microfluidic probe head for providing a sequence of separate liquid volumes separated by spacers, the separate liquid volumes in a respective target substance associated with a respective target area, the microfluidic probe head including an inlet and an outlet; a first fluid channel fluidly connected to the inlet, the first fluid channel being configured for delivering an injection liquid from the inlet to a respective target area, the respective target area being covered by an immersion liquid and including a respective target substance; a second fluid channel fluidly connected to the outlet, the second fluid channel being configured for delivering liquid volumes from the respective target area to the outlet, each liquid volume including at least some of the injection liquid, at least some of the immersion liquid and a respective target substance; and a spacer insertion unit fluidly connected to the second fluid channel, the spacer insertion unit being configured for inserting spacers into the second fluid channel between the liquid volumes to thereby provide the sequence of separate liquid volumes separated by spacers.

According to a second aspect, the invention can be embodied as a microfluidic probe include an inlet and an outlet; a first fluid channel fluidly connected to the inlet, the first fluid channel configured for delivering an injection liquid from the inlet to a respective target area, wherein, in operation, the respective target area is covered by an immersion liquid and includes a respective target substance; a second fluid channel fluidly connected to the outlet, the second fluid channel configured for delivering liquid volumes from the respective target area to the outlet, each liquid volume including at least some of the injection liquid, at least some of the immersion liquid and a respective target substance; a spacer insertion unit fluidly connected to the second fluid channel, the spacer insertion unit configured for inserting spacers into the second fluid channel between the liquid volumes to provide the sequence of separate liquid volumes separated by spacers; and a positioning device configured for positioning the microfluidic probe head above a respective target area.

According to a third aspect, the invention can be embodied as a method for providing a sequence of separate liquid volumes separated by spacers, the separate liquid volumes including a respective target substance associated with a respective target area, the method including delivering via a first fluid channel an injection liquid from an inlet to a respective target area, the respective target area being covered by an immersion liquid and including a respective target substance; delivering via a second fluid channel liquid volumes from the respective target area to an outlet, each liquid volume including at least some of the injection liquid, at least some of the immersion liquid and a respective target substance; and inserting spacers between the liquid volumes to thereby provide the sequence of separate liquid volumes separated by spacers.

DETAILED DESCRIPTION

Figure 1:
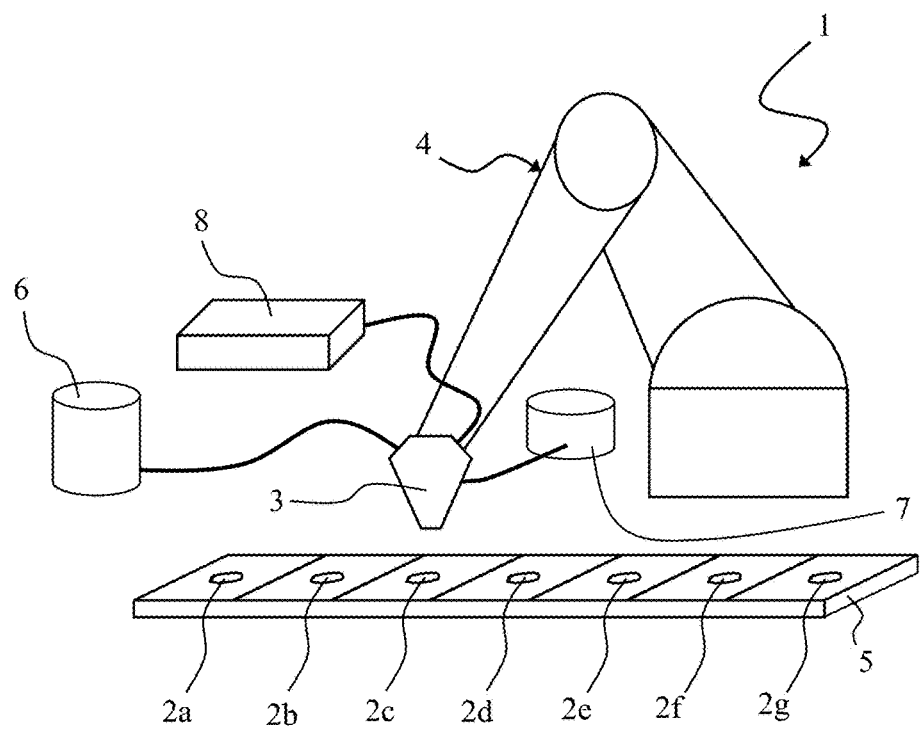
FIG. 1 shows, in a perspective view, a microfluidic probe including a microfluidic probe head.

FIG. 1 shows a perspective view of a microfluidic probe 1 for sequentially retrieving target substances from respective target areas 2a-2g using, preferably, hydrodynamic flow confinement.

Generally speaking, hydrodynamic flow confinement (HFC) relates to a phenomenon that a laminar flow of an injection liquid is spatially confined within a liquid bath containing another liquid. Embodiments of the invention can advantageously rely on hydrodynamic flow confinement, as discussed in detail below. For the sake of illustration, embodiments discussed herein mostly assume hydrodynamic flow confinement. For instance, in the embodiment of FIG. 2, an injection microchannel injects the injection liquid into the liquid bath with an injection flow rate and an aspiration microchannel aspirates the injection liquid and some of the background liquid with an aspiration flow rate. By keeping the aspiration flow rate higher than the injection rate at a defined ratio, the laminar flow of the injection liquid from the injection channel to the aspiration channel is formed and confined inside a volume within the surrounding liquid bath.

The microfluidic probe 1 includes a microfluidic probe head 3 attached to a positioning device, in particular to a robotic arm 4. Additionally, the microfluidic probe head 3 and/or the robotic arm 4 can be attached to a movable stage. The robotic arm 4 is configured for positioning the microfluidic probe head 3 at a specific location and, in particular, above each of the target areas 2a-2g that are arranged in an array 5. Preferably, the microfluidic probe 1 further includes an x, y and z positioning stage in order to perform an arbitrary three-dimensional movement.

An injection liquid supply 6, a spacer supply 7 and an analyzer 8 are fluidly connected to the microfluidic probe head 3. The injection liquid supply 6 provides the microfluidic probe head 3 with an injection liquid 20. The spacer supply 7 provides the microfluidic probe head 3 with a spacer fluid 23. The retrieved target substances are delivered from the microfluidic probe head 3 to the analyzer 8.

Figure 2:
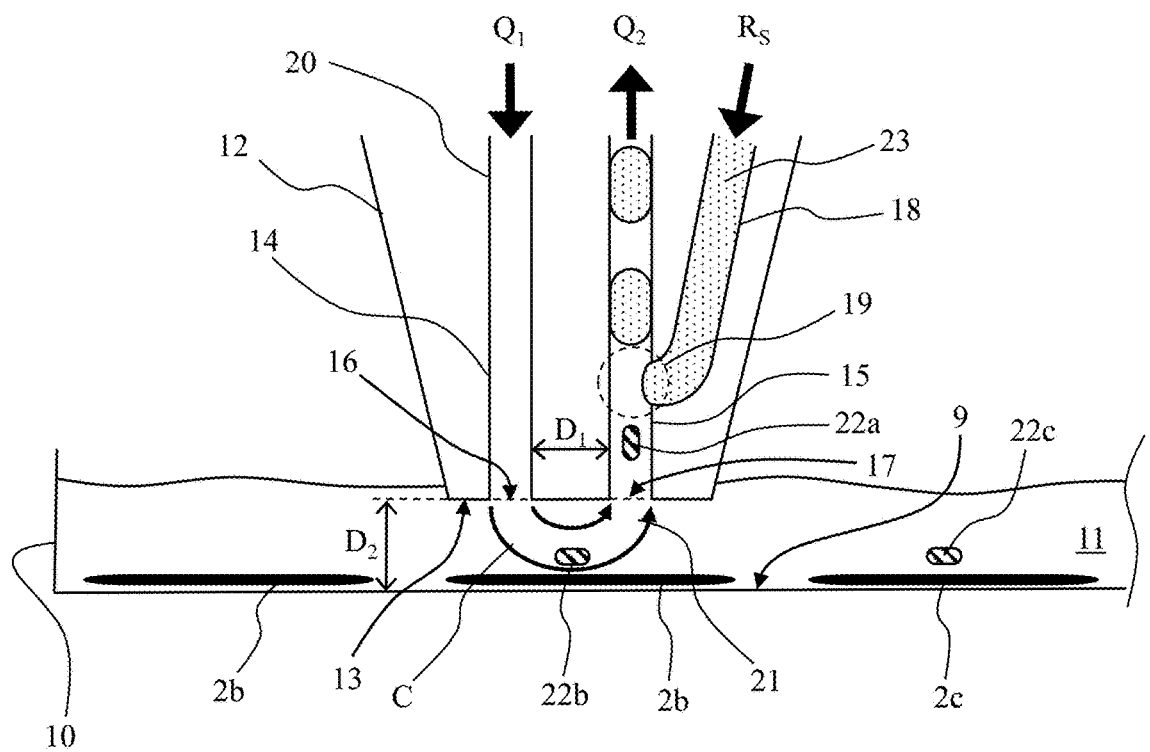
FIG. 2 shows a cross-sectional partial view of a first embodiment of the microfluidic probe head of FIG. 1.

FIG. 2 shows a cross-sectional partial view of a first embodiment of the microfluidic probe head 3 of FIG. 1.

In the embodiment of FIG. 2, the target areas 2a-2c are located on top of a bottom surface 9 of a Petri dish 10 or similar that is at least partly filled with an immersion liquid 11 such that the target areas 2a-2c are covered with the immersion liquid 11.

The microfluidic probe head 3 includes a body 12 having an end face 13. A first fluid channel 14 and a second fluid channel 15 are formed in the body 12. A first aperture 16 and a second aperture 17 are formed in the end face and fluidly connected to the first and second fluid channels 14, 15, respectively. For example, a distance $D_1$ between the first and second apertures can be 0.1 µm-10 mm, preferably 0.5 µm-2.0 mm and more preferably 1.0 µm-1.0 mm A spacer channel 18 is fluidly connected to the second fluid channel 15 at a spacer junction 19.

The body 12 of the microfluidic probe head 3 acts as housing or carrier. All elements, parts and/or devices integrated in the body 12 can be manufactured on-chip (using lithography, for example) and are movable therewith.

In FIG. 2, the microfluidic probe head 3 is positioned above the target area 2b. The end face 13 of the microfluidic probe head 3 spaced from the target are 2b such that the end face 13 is immersed in the immersion liquid 11 that covers the target areas 2a-2c. For example, a distance $D_2$ of the end face 13 from the target area 2b can be 1-100 µm, preferably 1.5-90 µm and more preferably 2-80 µm.

The injection liquid 20 is delivered via the first fluid channel 14 to the first aperture 16 with a first flow rate $Q_1$. An underpressure is applied to the second fluid channel 15 such that some of the immersion liquid 11 and the injection liquid 20 that is discharged into the immersion fluid 11 through the first aperture 16 are aspirated through the second aperture 17 with a second flow rate $Q_2$. For example, the first and second flow rates $Q_1$, $Q_2$ can be generated using corresponding pumps (not shown).

If the second flow rate $Q_2$ is higher than the first flow rate $Q_1$ with a specific ratio of the second flow rate $Q_2$ to the first flow rate $Q_1$, namely, for example, 1.2-10, preferably 1.5-6 and more preferably 2-4, a laminar flow C can be obtained from the first aperture 16 to the second aperture 17. Achieving such a laminar flow allows for hydrodynamic flow confinement. I.e. the laminar flow C is hydrodynamically confined by the immersion liquid 11 within a confinement volume 21 that extends from below the first aperture 16 to below the second aperture 17. The size of the confinement volume 21 and the shape of the laminar flow C are defined by, but not limited to, the first flow rate $Q_1$, the second flow rate $Q_2$ and the ratio of the second flow rate $Q_2$ to the first flow rate $Q_1$, the distance $D_1$ between the first and second apertures and/or the distance $D_2$ between the end face 13 and the respective target area 2a-2c. For example, the first flow rate $Q_1$ can be chosen to be 1.0 fL/s-1.0 mL/s, preferably 1.0 pL/s-100 nL/s and more preferably 1.0-50 nL/s. For Example, the second flow rate $Q_2$ is 1.2 fL/s-10 mL/s, preferably 2.0 pL/s-1.0 mL/s and more preferably 2.0-200 nL/s.

In FIG. 2, a target substance 22a has been carried away from the target area 2a by the laminar flow C and aspirated through the second aperture 17 into the second fluid channel 15. After retrieving the target substance 22a from the target area 2a, the microfluidic probe head 3 is positioned above the target area 2b such that the confinement volume 21 encases a target substance 22b located on top of the target area 2b. The target substance 22b can be carried away from the target area 2b by the laminar flow C and then, along with the laminar flow C, aspirated through the second aperture 17 into the second fluid channel 15. Subsequently, the microfluidic probe head 3 can be positioned above the target area 2c in order to retrieve a target substance 22c.

The steps of positioning the microfluidic probe head 3 above the target area 2a-2c and retrieving the target substance 22a-22c from the respective target area 2a-2c can be repeated as many times as required in order to retrieve a sequence of target substances separated by the spacers 24.

The target substances 22a-22c can include biochemical substances. In particular, the target substances 22a-22c can include at least a cell of a living organism and/or at least a part of a deoxyribonucleic acid (DNA), proteins, or other biological or chemical substances.

The spacer channel 18 delivers the spacer fluid 23 to the spacer junction 19 where the spacer fluid 23 is discontinuously inserted into the second fluid channel 15 with a spacer insertion rate $R_s$ as to form droplet-shaped spacers 24. Accordingly, aspirated fluids moving along the second fluid channel 15 are sectioned into separate liquid volumes 25 separated by the spacers 24.

The injection liquid 20 can include a polar liquid, in particular a water-based or water-soluble liquid. The spacer fluid 23 can include a fluid that is immiscible with the injection liquid 20 and the immersion liquid 11. In particular, the spacer fluid 23 can include a nonpolar liquid and/or nonpolar solvent, e.g. a fat, an oil, a lipid, hexane or toluene. Furthermore, it is possible that spacer fluid 23 is a gas.

Figure 3:
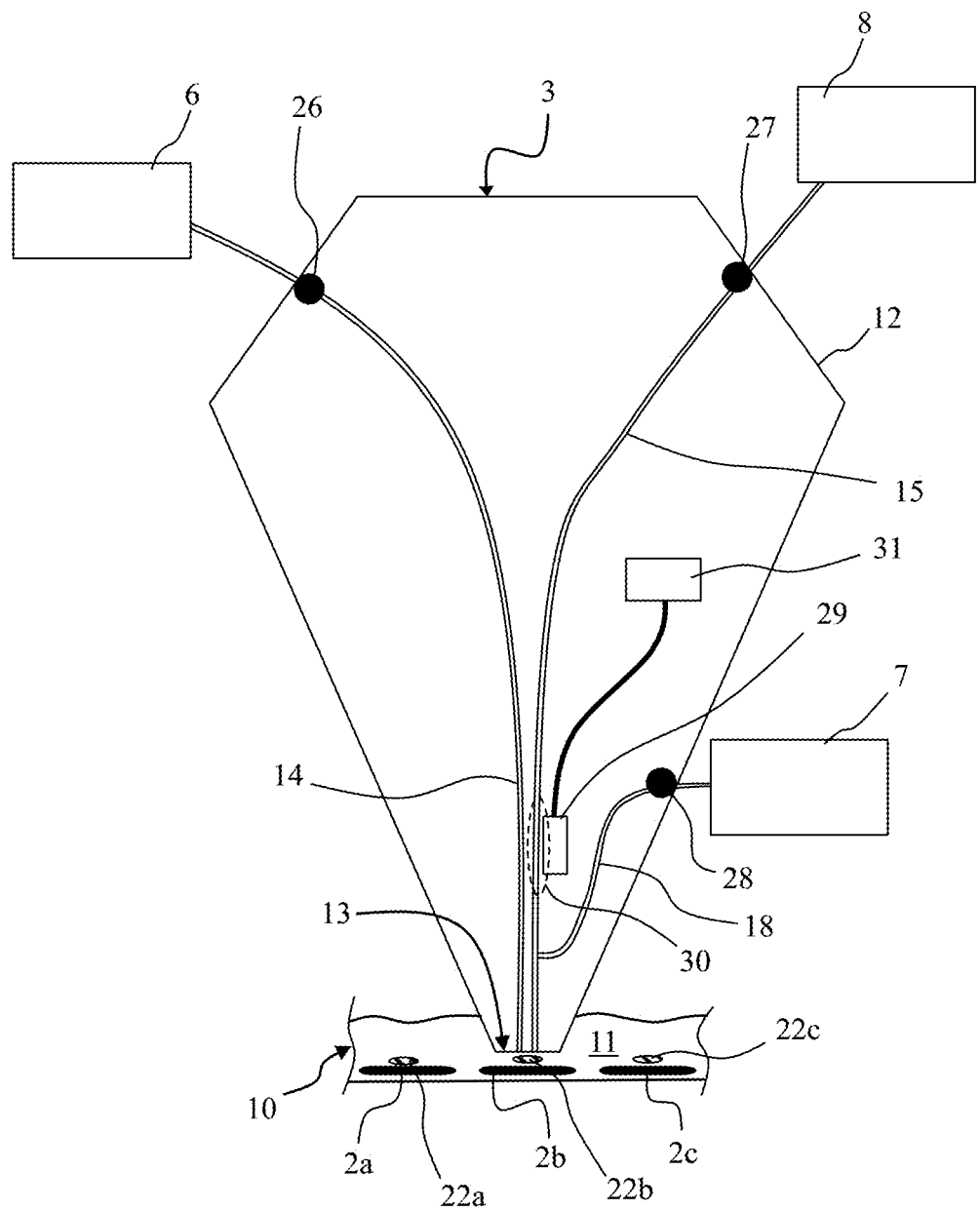
FIG. 3 shows a comprehensive view of the first embodiment of the microfluidic probe head and the fluid connections from FIG. 1.

FIG. 3 shows a comprehensive view of the first embodiment of the microfluidic probe head 3 and the fluid connections from FIG. 1.

An inlet 26 fluidly connects the first fluid channel 14 located inside the body 12 to the injection liquid supply 6 located outside of the body 12. An outlet 27 fluidly connects the second fluid channel 15 located inside the body 12 to the analyzer 8 located outside of the body 12. A spacer inlet 28 fluidly connects the spacer channel 18 located inside the body 12 to the spacer supply 7 located outside of the body 12.

A detection unit 29 is installed inside the body 12 of the microfluidic probe head 3. The detection unit 29 has a detection volume 30 inside the second fluid channel 15. The detection unit 29 can measure properties, e.g. a surface tension, a refraction index, a pH, a heat conductivity, an electrical conductivity, a viscosity, an impedance, a temperature and/or an inductance, of the separate liquid volumes 25 that pass through the identification volume 30 in order to identify the respective separate liquid volumes 25. In particular, measuring the properties of the separate liquid volumes 25 can be performed electrically, magnetically, optically, chemically, thermally and/or mechanically. Upon identifying the separate liquid volumes 25, the detection unit 29 generates a detection signal and transmits it to a spacer insertion unit 31 located inside the body 12. The spacer insertion unit 31 controls the insertion rate $R_s$, at which the spacers 24 are inserted into the second fluid channel 15.

In particular, the insertion rate $R_s$ can be synchronized with a positioning rate P, at which the microfluidic probe head 3 is positioned above each of the target areas 2a-2c in order to ensure that each of the separate liquid volumes 25 separated by spacers 24 contains exclusively the target substance 2a-2c from the respective target area 2a-2c. For example, the insertion rate $R_s$ is given as a number of spacers 24 inserted into the second fluid channel 15 in a given time interval T, and the positioning rate P is given as a number of target areas 2a-2c from which the microfluidic probe head 3 retrieves the respective target substances 22a-22c in the same time interval T. In this example, a synchronization of the insertion rate $R_s$ with the positioning rate P can be achieved by setting $R_s$ and P equal.

In accordance with another embodiment, a fixed insertion rate $R_s$ (independent of the current position of the microfluidic head) can be used, e.g. 10 ms. Preferably, this fixed insertion rate should be chosen smaller than the rate at which target substances are aspirated to ensure only a single (or none at all, as the case can be) target substance per separate liquid volume is provided. The relative position in two dimensions of the target substances is therefore easily translated into a series of liquid volumes separated by spacers.

The sequence of target substances 22a-22c, each enclosed in one of the separate liquid volumes 25, is delivered to the outlet 27 via the second fluid channel 15 and from the outlet 27 further to the analyzer 8. The analyzer 8 is, in particular, configured for analyzing the retrieved target substances 22a-22c in the separate liquid volumes 25 in terms of chemical and/or biological properties.

A cross-contamination of the target substances 22a-22c with one another is prevented by retrieving the target substances 22a-22c separated by the spacers 24.

Figure 4:
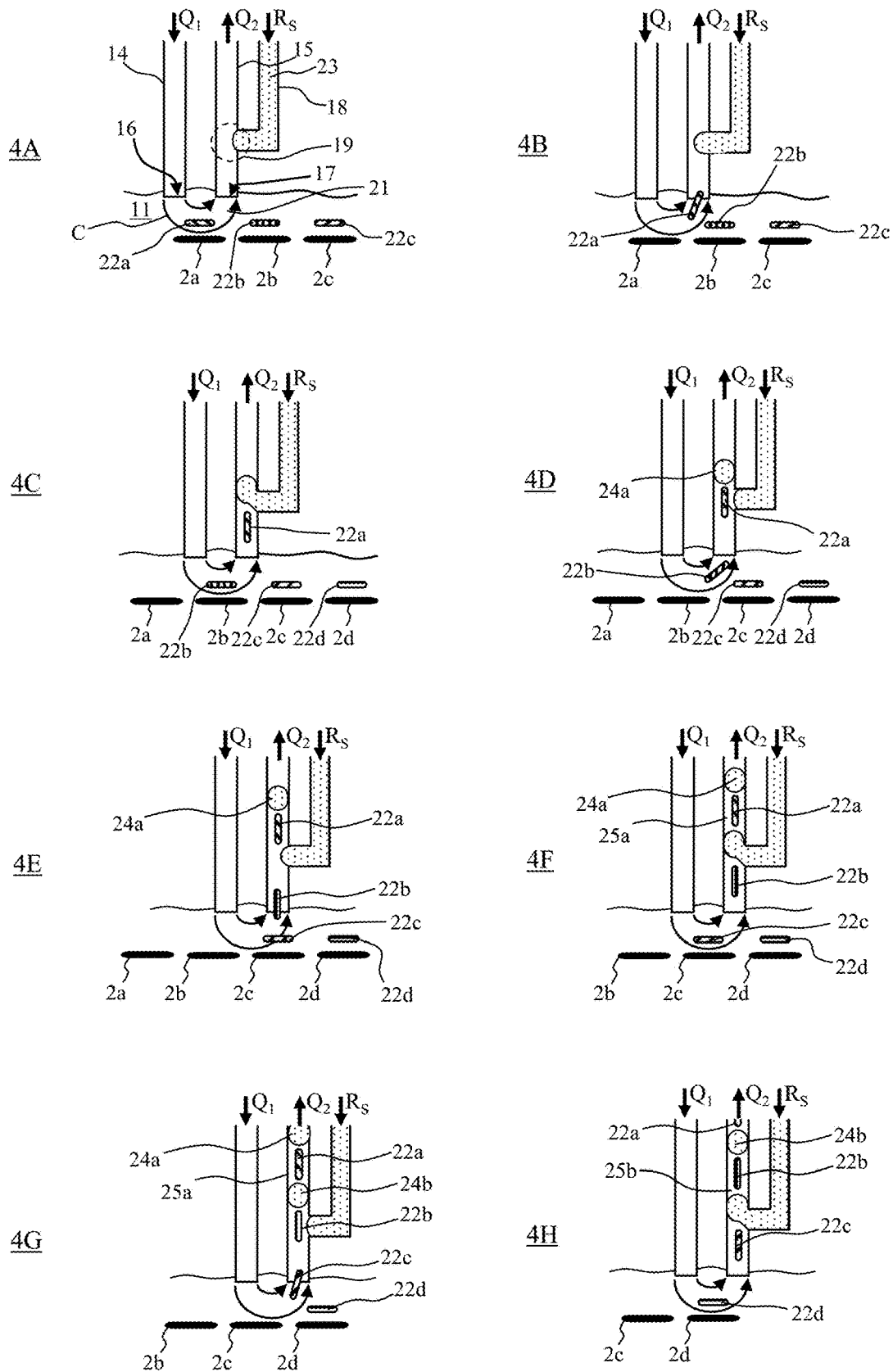
FIG. 4 illustrates subsequent operation steps of the microfluidic probe head from FIG. 2.

FIG. 4 includes eight operation steps, FIG. 4A-4H. FIG. 4A-4H illustrate subsequent operation steps of the microfluidic probe head 3 from FIG. 2. The Petri dish 10 and the body 12 of the microfluidic probe head 3 are not shown.

In FIG. 4A, the injection liquid 20 is delivered to the first aperture 16 via the first fluid channel 14 and discharges through the first aperture 16 into the immersion liquid 11 with the first flow rate $Q_1$. At the same time, an underpressure is applied to the second fluid channel such that liquids, both the injection liquid 20 discharged through the first aperture 14 and part of the immersion liquid 11 is aspirated through the second aperture 17 into the second fluid channel 15 with the second flow rate $Q_2$.

The target areas 2a-2c can be arranged, for example, in an array with a fixed distance from each other. Each of the target substances 22a-22c is attached to the respective target area 2a-2c immersed in the immersion liquid 11.

Due to the above described ratio of the second flow rate $Q_2$ to the first flow rate $Q_1$, the laminar flow C of the injection liquid from the first aperture 16 to the second aperture 17 is confined by the surrounding immersion liquid 11 within the confinement volume 21. The microfluidic probe head 3 is positioned above the target area 2a such that the respective target substance 22a is located inside the confinement volume 21.

In FIG. 4B, the target substance 22a is detached from the target area 2a by the laminar flow C. The target substance 22a is carried to the second aperture 17 and aspirated into the second fluid channel 15. In the meantime, the microfluidic probe head 3 is moved towards the next target area 2b.

At the same time, the spacer fluid 23 is inserted from the spacer channel 18 into the second fluid channel 15 at the spacer junction 19.

In FIG. 4C, the target substance 22a has completely been aspirated into the second fluid channel 15 and moves upwards along the second fluid channel 15. Downstream of the target substance 22a in the second fluid channel 15, a constriction emerges between an inserted part of the spacer fluid 23 in the second fluid channel 15 and a remaining part of the spacer fluid 23 in the spacer channel 18.

In the meantime, the microfluidic probe head 3 is positioned above the target area 2b such that the respective target substance 22b is located inside the confinement volume 21.

In FIG. 4D, the inserted part of the spacer fluid 23 is cut off from the remaining part of the spacer fluid 23 and forms a droplet-shaped first spacer 24a. The first spacer 24a divides the aspirated fluids into two parts, upstream and downstream of itself, inside the second fluid channel 15. The first spacer 24a moves along the second fluid channel 15 with the second flow rate $Q_2$.

The target substance 22b has been detached from the respective target area 2b by the laminar flow C and is carried towards the second aperture 17. The microfluidic probe head 3 is moved towards the target area 2c.

In FIG. 4E, the target substance 22a and the preceding first spacer 24a move along the second fluid channel 15 with the second flow rate $Q_2$. The spacer fluid 23 is continuously inserted into the second fluid channel 15. The target substance 22b enters the second fluid channel 15 and moves upwards along the second fluid channel 15 with the flow rate $Q_2$.

In FIG. 4F, the spacer fluid 23 is inserted into the second fluid channel 15 to such an extent that, again, a constriction emerges in the second fluid channel 15 between the inserted part and the remaining part of the spacer fluid 23. The inserted part of the spacer fluid 23 is located between the target substances 22a and 22b and encloses a first liquid volume 25a that contains the target substance 22a.

The microfluidic probe head 3 is positioned above the target area 2c and the respective target substance 22c is located inside the confinement volume 21.

In FIG. 4G, the inserted part of the spacer fluid 23 is cut off from the remaining part, thereby forming a second spacer 24b between the target substances 22a and 22b in the second fluid channel 15. The target substances 22a, 22b, the first liquid volume 25a and the first and second spacers 24a, 24b move along the second fluid channel 15 with the second flow rate $Q_2$.

In the meantime, the target substance 22c has been detached from the respective target area 2c and carried to the second aperture 17. The target substance 22c is aspirated through the second aperture 17 into the second fluid channel 15. Furthermore, the microfluidic probe head 3 is moved towards the target area 2d.

In FIG. 4H, the target substance 22c moves along the second fluid channel 15 with the second flow rate $Q_2$. A third spacer is about to be formed between the target substances 22b, 22c. A second liquid volume 25b is enclosed by the preceding second spacer 24b and the inserted part of the spacer fluid 23. The microfluidic probe head 3 is positioned above the target area 2d and the respective target substance 22d is located inside the confinement volume 21.

By repeating the above described operation steps, a sequence of separate liquid volumes can be formed, with the separate liquid volumes separated from one another by the spacers and each liquid volume containing the target substance from the respective target area.

The spacers can advantageously prevent the liquid volumes and/or target substances from spreading, diffusing and/or mixing with one another. In particular, convective and/or diffusive spreading of the liquid volumes can be prevented. At the same time, dilution of the retrieved target substances (also referred to as analytes) within a respective liquid volume is minimized Another advantage is that the temporal and/or spatial information about a respective target substance, i.e. its point of origin on a surface (or, more generally, in space), is retained. This information can be used to allocate the respective target substance to a respective target area. In embodiments, the spacer insertion unit is configured for inserting the spacers into the second fluid channel with an insertion rate, and the insertion rate is synchronized with the positioning of the microfluidic probe head by the positioning device.

Figure 5:
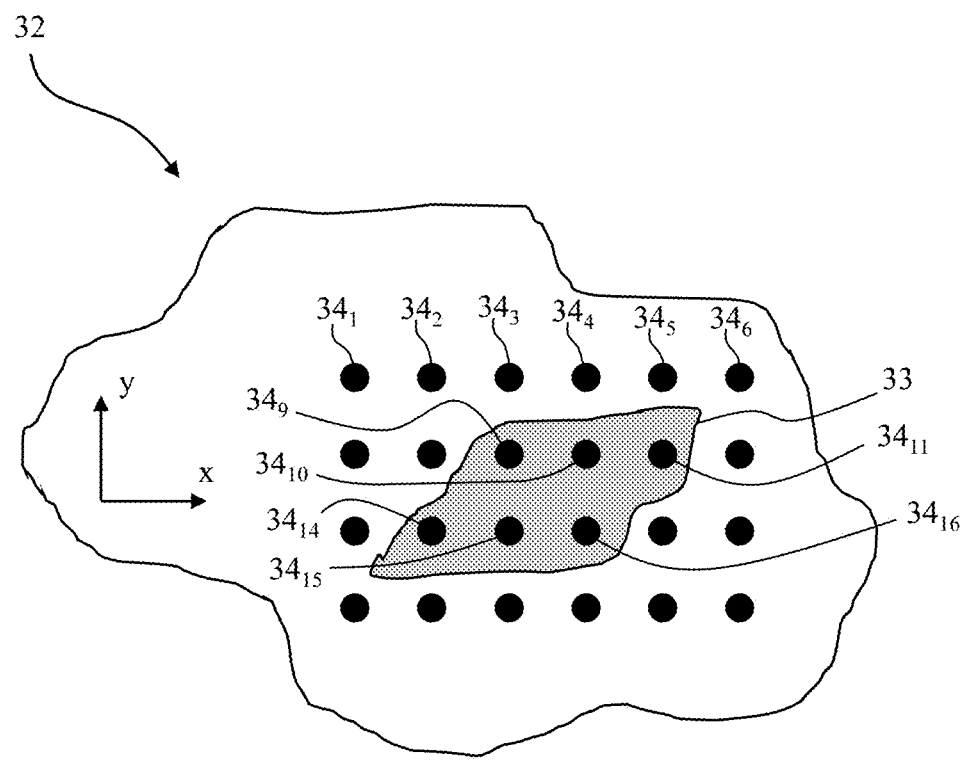
FIG. 5 shows a schematic view of a part of a tissue section including tumorous cells.

FIG. 5 shows a schematic view of a tissue section 32 containing a tumorous area 33.

An array of target areas $34_1$-$34_{24}$ is arranged on a surface of the tissue section 32 including the tumorous area 33. The microfluidic probe head 3 retrieves samples from each of the target areas $34_1$-$34_{24}$ and delivers them to the analyzer 8. For example, the analyzer 8 is configured for determining a ratio $R_T$ of tumorous cells to healthy cells of each of the samples and allocating the ratio to the respective target area $34_1$-$34_{24}$. This facilitates a spatial mapping and a localization of the tumorous cells in the tissue section 32. According to the example, the samples from the target areas $34_9$-$34_{11}$, $34_{14}$-$34_{16}$ that are located in the tumorous area 33 would show a high $R_T$, whereas the samples from outside of the tumorous area 33 would result in a low $R_T$. In this way, a cancer heterogeneity in terms of the spatial distribution can be investigated and/or a progression front of tumor can be investigated.

The spatial mapping and localization using the microfluidic probe head 3 is not limited to cancer/tumor research, but can be applied to any other analytes by selecting the biochemical species to be retrieved by the microfluidic probe head 3 and by varying a analyze method of the retrieved species. As an example, a precise localization of DNA and single cells in a micro-array, i.e. a system of regularly arranged samples, analytes, and/or other (bio)chemical substances, can be performed using the microfluidic probe head 3.

Figure 6:
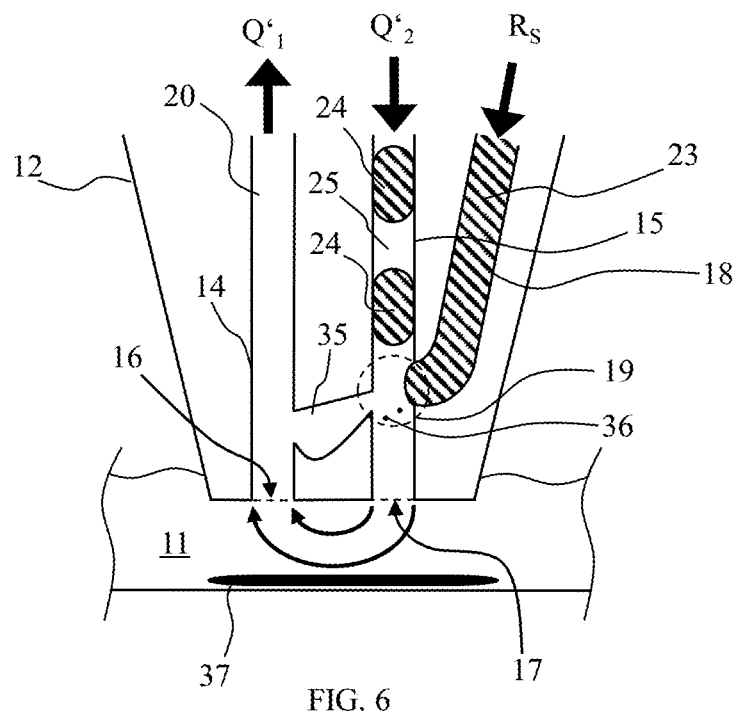
FIG. 6 shows a cross-sectional partial view of a second embodiment of the microfluidic probe head of FIG. 1.

FIG. 6 shows a cross-sectional partial view of a second embodiment of the microfluidic probe head 35 of FIG. 1.

The microfluidic probe head 3 has a similar structure similar to the microfluidic probe 3 from FIG. 2. Additionally, the microfluidic probe head 3 includes a fluid bypass 35 that fluidly connects the first and second fluid channels 14, 15 to each other and blocking elements 36 that is configured for redirecting the spacers 24 into the fluid bypass 35.

Furthermore, in comparison to the microfluidic probe head 3 of FIG. 2, the first and second flow rates $Q_1$, $Q_2$ can be changed. The microfluidic probe head 35 has a reversed operation mode for depositing a sequence of separate liquid volumes 25 (including substances to be deposited; herein also referred to as "target substance") in addition to a normal operation mode of retrieving target substances that is described by means of the microfluidic probe head 3 of FIG. 2. In the second operation mode, flow directions of the first operation mode, namely from the inlet 26 towards the first aperture 16 in the first fluid channel 14 and from the second aperture towards the outlet 27 in the second fluid channel 15, can be reversed such that liquids in the first fluid channel 14 flow towards the inlet 26, and liquids in the second fluid channel 15 flow towards the second aperture 17.

A sequence of separate liquid volumes 25 separated by the spacers 24 is delivered to the second aperture 17 with a reversed second flow rate $Q'_2$. At the first aperture 16, the liquid volumes and part of the immersion liquid 11 are aspirated into the first fluid channel 14 with a reversed first flow rate $Q'_1$. The reversed first flow rate Q'1 is greater than the reversed second flow rate $Q'_2$, and a ratio of the reversed first flow rate Q'1 to the reversed second flow rate $Q'_2$ can be chosen to be, for example, 1.2-10, preferably 1.5-6 and more preferably 2-4. For example, the reversed first flow rate $Q'_1$ can be 0.2 fL/s-4.0 mL/s, preferably 2.0 pL/s-400 nL/s and more preferably 2.0-200 nL/s. For example, the reversed second flow rate $Q'_2$ can be 1.0 fL/s-1.0 mL/s, preferably 1.0 pL/s-100 nL/s, more preferably 1.0-50 nL/s. Under this conditions, a reversed laminar flow C' is formed from the second aperture 17 to the first aperture 16 and confined by the immersion liquid 11 within a reversed confinement volume 21'. Again, achieving such a laminar flow allows for hydrodynamic flow confinement.

By positioning the microfluidic probe head 3 above a deposition area 37 such that the reversed confinement volume 21' is in surface contact with the deposition are 37, a part of the liquid volume 25 that passes through the confinement volume 21' with the reversed laminar flow C' can adhere to the deposition area 37. By repeating the steps of positioning the microfluidic probe head 3 and feeding the sequence of separate liquid volumes 25 through the reversed confinement volume 21', the separate liquid volumes 25 can be deposited on the respective deposition areas.

The blocking elements 36 redirect the spacers 24 that separate the separate liquid volumes 25 of the sequence of liquid volumes 25 from one another into the fluid bypass 35 and thereby prevents the spacers 24 from reaching the second aperture 17 and discharging into the immersion liquid 11.

If the spacers 24, in particular spacers that include an oil-phase, come into contact with the deposition area 37, surface properties of the deposition area 37 can be altered and the deposition area 37 can be contaminated and the stability of the hydrodynamic flow confinement can be disrupted, thereby disturbing the deposition of the liquid volumes at the required deposition area 37. In particular, biochemical substances such as proteins, cells and biological tissues on the deposition area 37 might be denatured and/or damaged by coming in contact with the spacers 24. On the other hand, lipophilic analytes such as lipids, therapeutic molecules, hormones, non-polar dyes or tracers can be carried away by the spacers 24. Furthermore, if the spacers 24 that are discharged through the first aperture 16 they can exert a shear stress on objects below and thereby damage and/or shift them.

Preferably, the method for providing a sequence of separate liquid volumes separated by spacers includes, in a first mode delivering the injection liquid from the inlet to the respective target area, delivering the liquid volumes from the respective target area to the outlet, and inserting the spacers between the liquid volumes to thereby provide the sequence of separate liquid volumes separated by spacers. In a second mode: delivering via the second fluid channel a sequence of separate liquid volumes separated by spacers from the outlet toward the respective target area, removing from the second fluid channel the spacers separating the separate liquid volumes from one another, via a fluid bypass that connects the first fluid channel and the second fluid channel, and thereby obtain a free sequence of separate liquid volumes, without spacers, delivering the free sequence of separate liquid volumes to the respective target area, and delivering the removed spacers from the fluid bypass to the inlet via the first fluid channel.

In preferred embodiments, delivering the injection liquid, delivering the liquid volumes, and inserting the spacers is carried out using a microfluidic probe head according to embodiments such as described above.

More generally, while the present invention has been described with reference to certain embodiments, it will be understood by those skilled in the art that various changes can be made and equivalents can be substituted without departing from the scope of the present invention. In addition, many modifications can be made to adapt a particular situation to the teachings of the present invention without departing from its scope. Therefore, it is intended that the present invention not be limited to the particular embodiments disclosed, but that the present invention will include all embodiments falling within the scope of the appended claims.

What is claimed is:

1. A method for providing a sequence of separate liquid volumes separated by spacers using a microfluidic probe head, the method comprising:
   delivering, via a first fluid channel fluidly connected to an inlet of the microfluidic probe head, an injection liquid from the inlet to a respective target area, the respective target area is covered by an immersion liquid and comprises a respective target substance positioned below the microfluidic probe head;
   delivering, via a second fluid channel fluidly connected to an outlet of the microfluidic probe head, liquid volumes from the respective target area to the outlet, each liquid volume including at least some of the injection liquid, at least some of the immersion liquid and the respective target substance;
   inserting, via a spacer insertion unit fluidly connected to a spacer channel, spacers into the second fluid channel between the liquid volumes to provide the sequence of separate liquid volumes separated by spacers; and
   detecting, via a detection unit installed inside the microfluidic probe head and connected to the spacer insertion unit, the respective target substance;
   identifying, via a detection volume fluidly connected to the detection unit and located inside the second fluid channel, the sequence of separate liquid volumes passing through the detection volume; and
   upon identifying the sequence of separate liquid volumes, generating by the detection unit a detection signal to be transmitted to the spacer insertion unit.

2. The method of claim 1, further comprising:
   in a first operation mode, delivering the injection liquid from the inlet to the respective target area, delivering the liquid volumes from the respective target area to the outlet, and inserting the spacers between the liquid volumes to thereby provide the sequence of separate liquid volumes separated by spacers;
   in a second operation mode, delivering via the second fluid channel a sequence of separate liquid volumes separated by spacers from the outlet toward the respective target area;
   removing from the second fluid channel the spacers separating the separate liquid volumes from one another, via a fluid bypass that connects the first fluid channel and the second fluid channel, and thereby obtain a free sequence of separate liquid volumes, without spacers;
   delivering the free sequence of separate liquid volumes to the respective target area; and
   delivering the removed spacers from the fluid bypass to the inlet via the first fluid channel.

3. The method of claim 2, further comprising:
   in the first operation mode, retrieving the respective target substance from the respective target area; and
   in the second operation mode in which a direction of flow through the microfluidic probe head is reversed, depositing the respective target substance at the respective target area.

4. The method of claim 1, further comprising:
   delivering the injection liquid from the inlet to the respective target area through a first aperture of the microfluidic probe head fluidly connected to the first fluid channel using a first flow rate; and
   delivering the liquid volumes from the respective target area to the outlet through a second aperture of the microfluidic probe head fluidly connected to the second fluid channel using a second flow rate, the second flow rate being greater than the first flow rate so as to confine the liquid volumes within the immersion liquid, and a ratio of the second flow rate to the first flow rate corresponds to a laminar flow from the first aperture to the second aperture.

5. The method of claim 1, further comprising:
   allocating, via an allocation unit, a respective detected target substance to a respective target area.

6. The method of claim 5, further comprising:
   inserting the spacers as a function of an allocation signal generated by the allocation unit.

7. The method of claim 6, wherein the spacers are inserted using a fixed insertion rate.

8. The method of claim 1, wherein the respective target substances are biochemical substances.

9. The method of claim 8, wherein the respective target substances include at least a cell of a living organism.

10. The method of claim 8, wherein the respective target substances include deoxyribonucleic acids (DNA).

11. The method of claim 1, wherein the spacers are immiscible with the injection liquid, the immersion liquid and the respective target substances.

12. The method of claim 1, further comprising:
   positioning, via a positioning device, the microfluidic probe head above the respective target area;
   inserting the spacers into the second fluid channel with an insertion rate; and synchronizing the insertion rate with the positioning of the microfluidic probe head by the positioning device.

13. The method of claim 1, further comprising:
measuring properties of the separate liquid volumes, the properties comprising: a surface tension, a refraction index, a pH, a heat conductivity, an electrical conductivity, a viscosity, an impedance, a temperature and an inductance of the separate liquid volumes in order to identify the respective separate liquid volumes.

14. The method of claim 13, wherein the properties of the separate liquid volumes are measured electrically, magnetically, optically, chemically, thermally or mechanically.

15. The method of claim 1, wherein the spacers are discontinuously inserted into the second fluid channel at an insertion rate as to form droplet-shaped spacers.

* * * * *